US011116506B2

(12) United States Patent
Smith et al.

(10) Patent No.: US 11,116,506 B2
(45) Date of Patent: Sep. 14, 2021

(54) PARTIAL EVERSION ANASTOMOSIS JUNCTURE FORMATION AND SUTURING

(71) Applicant: Spiration, Inc., Redmond, WA (US)

(72) Inventors: Adam Lee Smith, Palm Desert, CA (US); Clifton A. Alferness, Olalla, WA (US); Gina M. Muia-Longman, Seattle, WA (US); Clinton L. Finger, Bellevue, WA (US); David R. Seward, Seattle, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 219 days.

(21) Appl. No.: 16/367,160

(22) Filed: Mar. 27, 2019

(65) Prior Publication Data

US 2019/0343527 A1    Nov. 14, 2019

Related U.S. Application Data

(60) Provisional application No. 62/668,696, filed on May 8, 2018, provisional application No. 62/676,452, filed on May 25, 2018.

(51) Int. Cl.
*A61B 90/00*    (2016.01)
*A61B 17/04*    (2006.01)
(Continued)

(52) U.S. Cl.
CPC ...... *A61B 17/1152* (2013.01); *A61B 17/0469* (2013.01); *A61B 17/11* (2013.01);
(Continued)

(58) Field of Classification Search
CPC .. A61B 2017/1121; A61B 2017/00252; A61B 2017/1135; A61B 2017/1132;
(Continued)

(56) References Cited

U.S. PATENT DOCUMENTS 6,015,416 A * 1/2000 Stefanchik ............. A61B 17/11
606/1
6,514,263 B1 2/2003 Stefanchik et al.
(Continued)

OTHER PUBLICATIONS

Assessment of Patented Coronary End-to-Side Anastomotic Devices Using MicromechanicalBonding.

*Primary Examiner* — Kathleen S Holwerda
*Assistant Examiner* — Lauren Dubose
(74) *Attorney, Agent, or Firm* — Clements Bernard Walker; Frank J. Bozzo

(57) ABSTRACT

Disclosed embodiments include apparatuses, systems, and methods for facilitating surgical anastomosis between bodily passages. In an illustrative embodiment, an eversion mechanism is configured to partially evert a distal portion of an opening of a receiving passage and further configured to leave a proximal portion of the opening of the receiving passage in a non-everted position. A donor support mechanism is configured to partially evert a distal portion of an opening at an end of a donor passage and further configured to leave a first proximal portion of the end of the donor passage in a non-everted position. The donor support mechanism is further configured to form a passage juncture at the end of the donor passage and the opening of the receiving passage. A suturing mechanism is configured to motivate a filament through a generally helical path around the passage juncture to suture the donor passage to the receiving passage.

12 Claims, 12 Drawing Sheets

(51) Int. Cl.
*A61B 17/11* (2006.01)
*A61B 17/00* (2006.01)
*A61B 17/115* (2006.01)

(52) U.S. Cl.
CPC ............ *A61B 90/361* (2016.02); *A61B 90/37* (2016.02); *A61B 2017/00566* (2013.01); *A61B 2017/1107* (2013.01); *A61B 2017/1121* (2013.01); *A61B 2017/1125* (2013.01); *A61B 2017/1132* (2013.01)

(58) Field of Classification Search
CPC .... A61B 2017/1125; A61B 2017/1139; A61B 2017/06076; A61B 17/11; A61B 90/37
See application file for complete search history.

(56) References Cited

U.S. PATENT DOCUMENTS

| | | | |
|---|---|---|---|
| 6,530,932 B1 | 3/2003 | Swayze et al. | |
| 6,613,058 B1 | 9/2003 | Goldin | |
| 2003/0153931 A1* | 8/2003 | Schraft | A61B 17/11 606/153 |
| 2006/0030869 A1* | 2/2006 | Loshakove | A61B 17/00491 606/153 |
| 2010/0181363 A1* | 7/2010 | Yasuda | A61B 17/115 227/180.1 |

* cited by examiner

PARTIAL EVERSION ANASTOMOSIS JUNCTURE FORMATION AND SUTURING

PRIORITY CLAIM

The present application claims the priority and benefit of U.S. Provisional Patent Application Ser. No. 62/668,696 for "SYSTEMS AND METHODS FOR PERFORMING CORONARY ARTERY BYPASS GRAFTING" filed May 8, 2018, and U.S. Provisional Patent Application Ser. No. 62/676,452 for "SYSTEMS AND METHODS FOR PERFORMING CORONARY ARTERY BYPASS GRAFTING" filed May 25, 2018.

FIELD

The present disclosure relates to apparatuses, systems, and methods for presenting and joining an opening of a donor passage to an opening in a receiving passage.

BACKGROUND

The statements in this section merely provide background information related to the present disclosure and may not constitute prior art.

Surgical anastomosis enables segments of one or more arteries, blood vessels, intestines, or any other passages to be connected or reconnected, such as in coronary artery bypass graft (CABG) procedures. In a CABG procedure, for example, a saphenous vein may be harvested from a patient's leg and grafted to circumvent a coronary arterial blockage. Such procedures are tremendously useful and may regularly save and extend lives.

However, CABG procedures and similar procedures involve highly invasive surgery. For example, a typical CABG procedure involves performing a median sternotomy in which a vertical incision is made along the patient's sternum, after which the sternum itself is actually broken open to provide access to the heart and surrounding arteries. The median sternotomy provides a surgeon with space to insert a graft and suture the graft to a coronary artery to complete the process. However, the sizable incision and the breaking of the sternum may involve significant scarring, discomfort, and risk of infection, and may require significant recovery time for the healing of the affected structures.

In addition, in the case of CABG and other procedures, consideration should be given to how grafts should be formed based on the intended location in a body. For example, based on an effect that various types of grafts may have on blood flow or circulation of other fluids in a body, different graft configurations may prove more suitable in some situations than in others.

SUMMARY

Disclosed embodiments include apparatuses, systems, and methods for facilitating surgical anastomosis between bodily passages, such as veins, arteries or other passages.

In an illustrative embodiment, an apparatus includes an eversion mechanism configured to partially evert a distal edge of an opening of a receiving passage and further configured to leave a proximal edge of the opening of the receiving passage in a non-everted position. A donor support mechanism is configured to partially evert a distal portion of an end of a donor passage and further configured to leave a proximal portion of the end of the donor passage in a non-everted position. The donor support mechanism is further configured to form a passage juncture at the end of the donor passage and the opening of the receiving passage. A suturing mechanism is configured to motivate a filament through a generally helical path around the passage juncture to suture the end of the donor passage to the receiving passage.

In another illustrative embodiment, a system includes a support body configured to be inserted into a body. A camera system is operably coupled with the support body, wherein the camera system is configured to convey imaging data from the support body to an operator. An eversion mechanism is configured to partially evert a distal edge of an opening of a receiving passage and further configured to leave a proximal edge of the opening of the receiving passage in a non-everted position. A donor support mechanism is configured to partially evert a distal portion of an end of a donor passage and further configured to leave a proximal portion of the end of the donor passage in a non-everted position. The donor support mechanism is further configured to form a passage juncture at the end of the donor passage and the opening of the receiving passage. A suturing mechanism is configured to motivate a filament through a generally helical path around the passage juncture to suture the donor passage to the receiving passage.

In a further illustrative embodiment, a method includes everting a distal portion of an end of the donor passage, with a proximal portion of the end of the donor passage remaining in a non-everted position. A distal edge of an opening of a receiving passage is everted, with a proximal edge of the opening of the receiving passage remaining in a non-everted position. A passage juncture is formed by placing the end of the donor passage adjacent to the opening of the receiving passage. A filament is motivated along a generally helical path around the passage juncture to suture the donor passage to the receiving passage.

Further features, advantages, and areas of applicability will become apparent from the description provided herein. It will be appreciated that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

Figure 1:
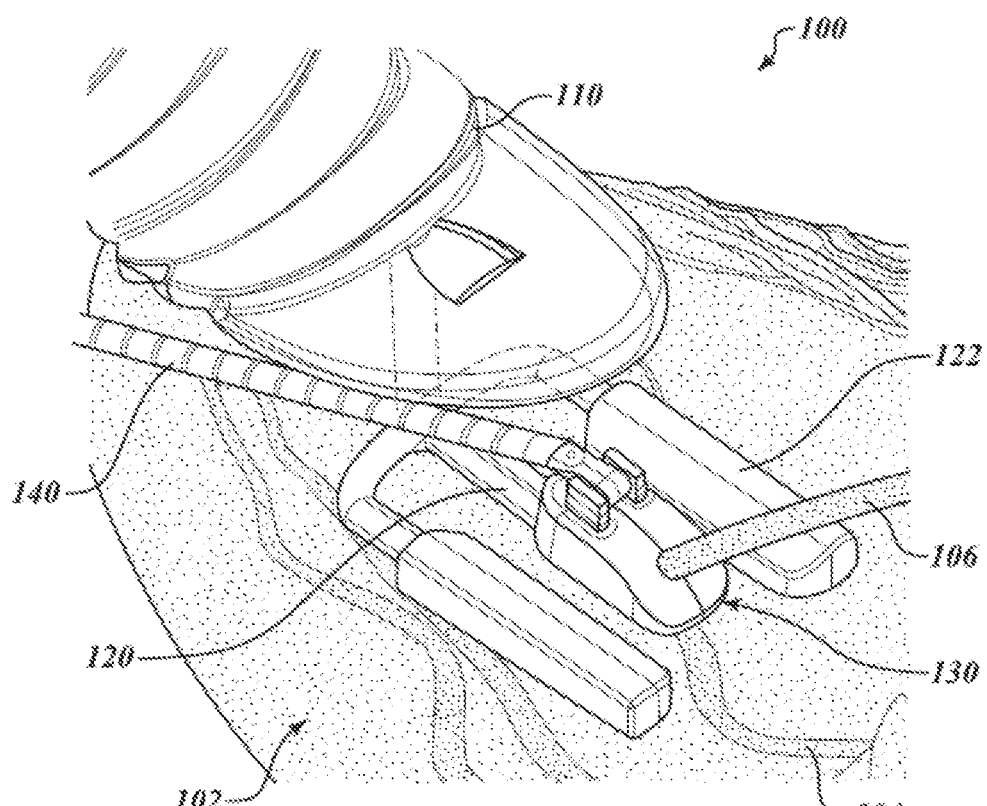
FIG. 1 is a perspective view of an illustrative system positioned on a heart for performing an illustrative CABG procedure.
Figure 2:
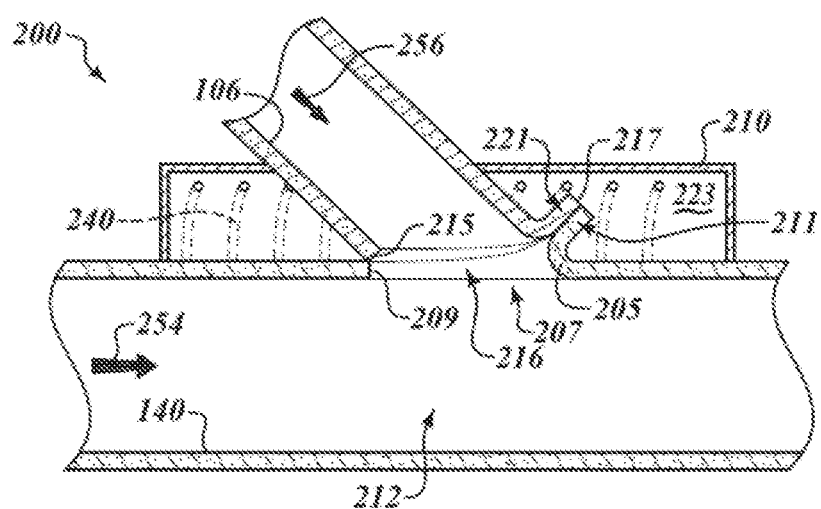
FIG. 2 is a perspective view in partial cutaway form of a suturing mechanism disposed to suture a passage juncture formed by an end of a donor passage and a receiving passage.
Figure 5A:
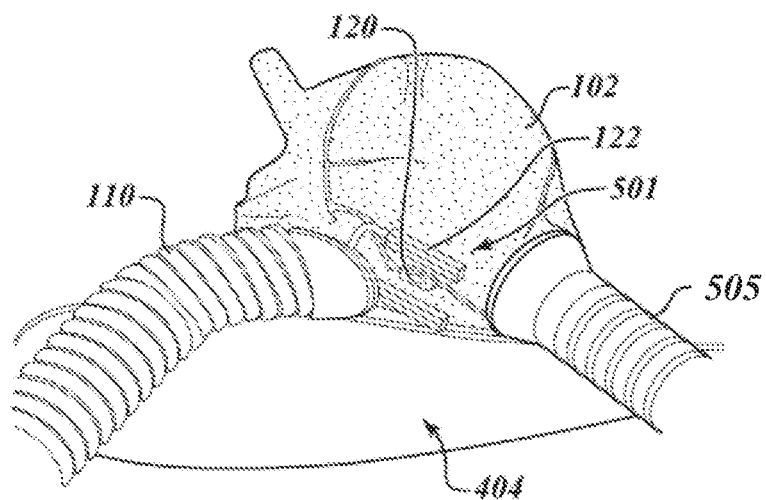
Figure 5B:
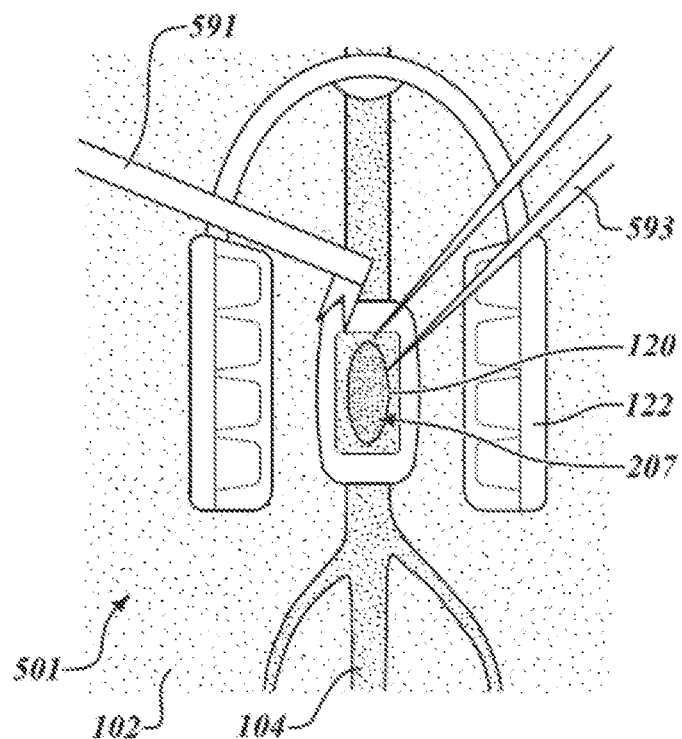
Figure 6A:
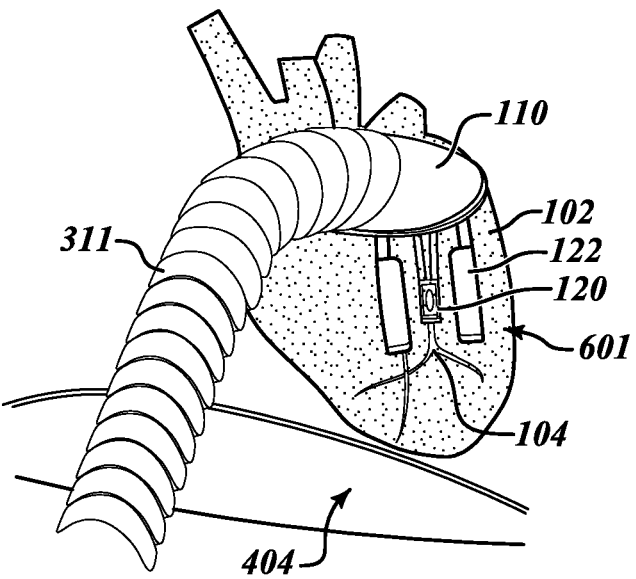
Figure 6B:
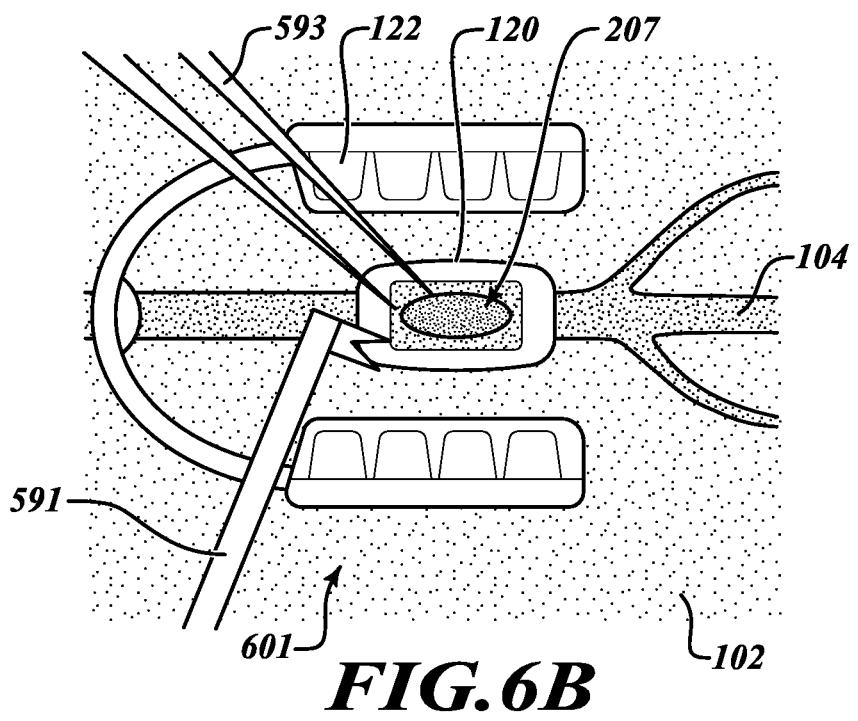
Figure 7A:
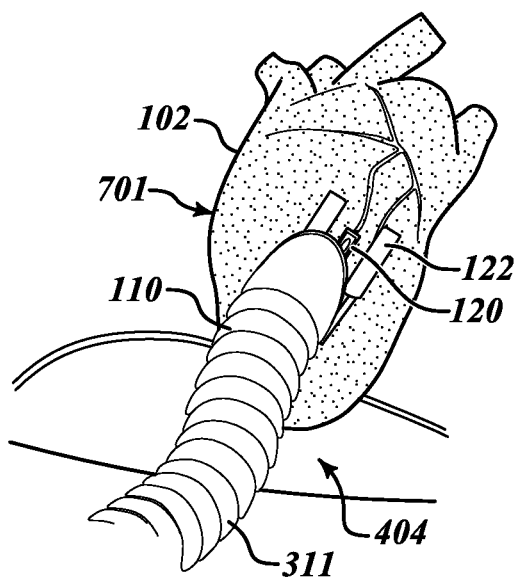
Figure 7B:
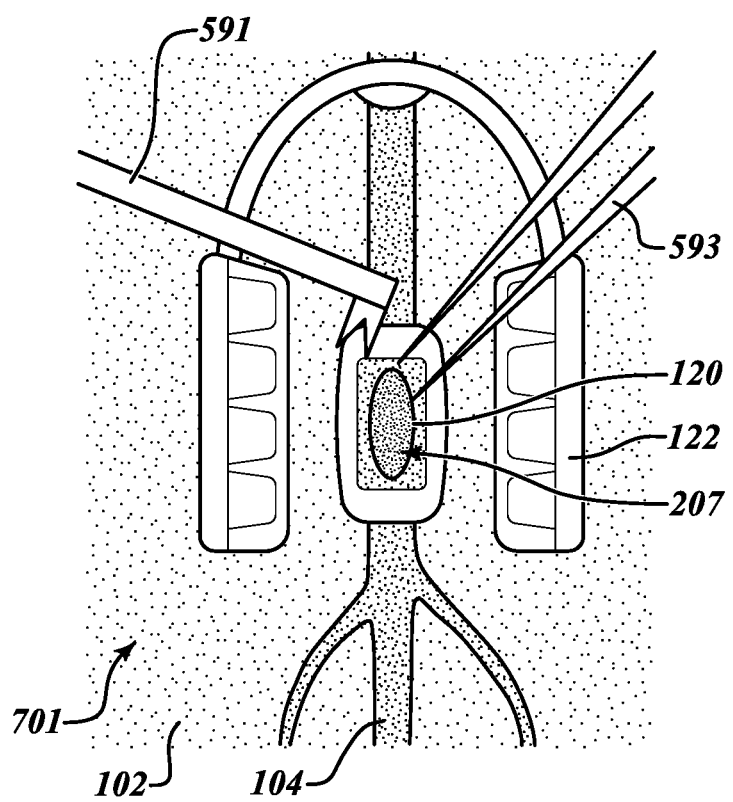
Figure 8:
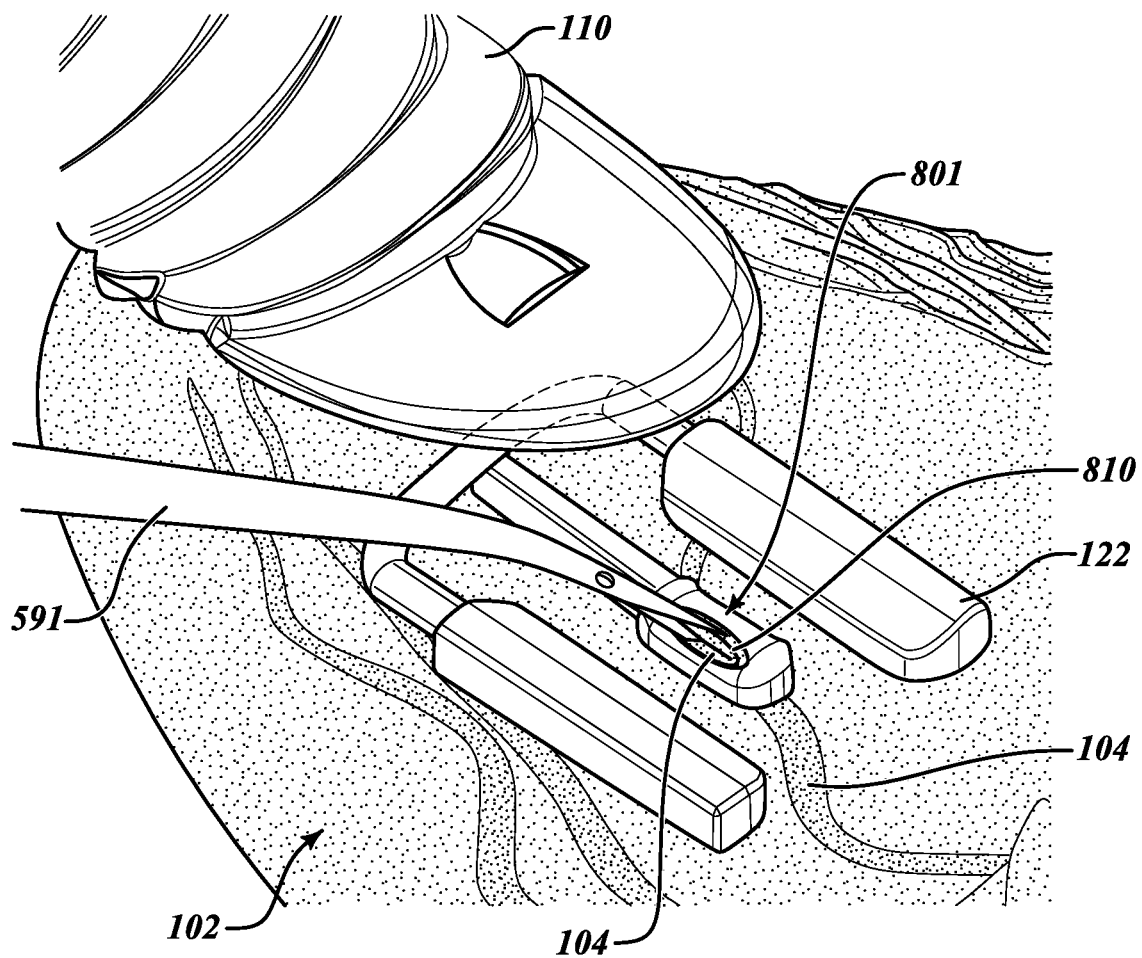
Figure 9A:
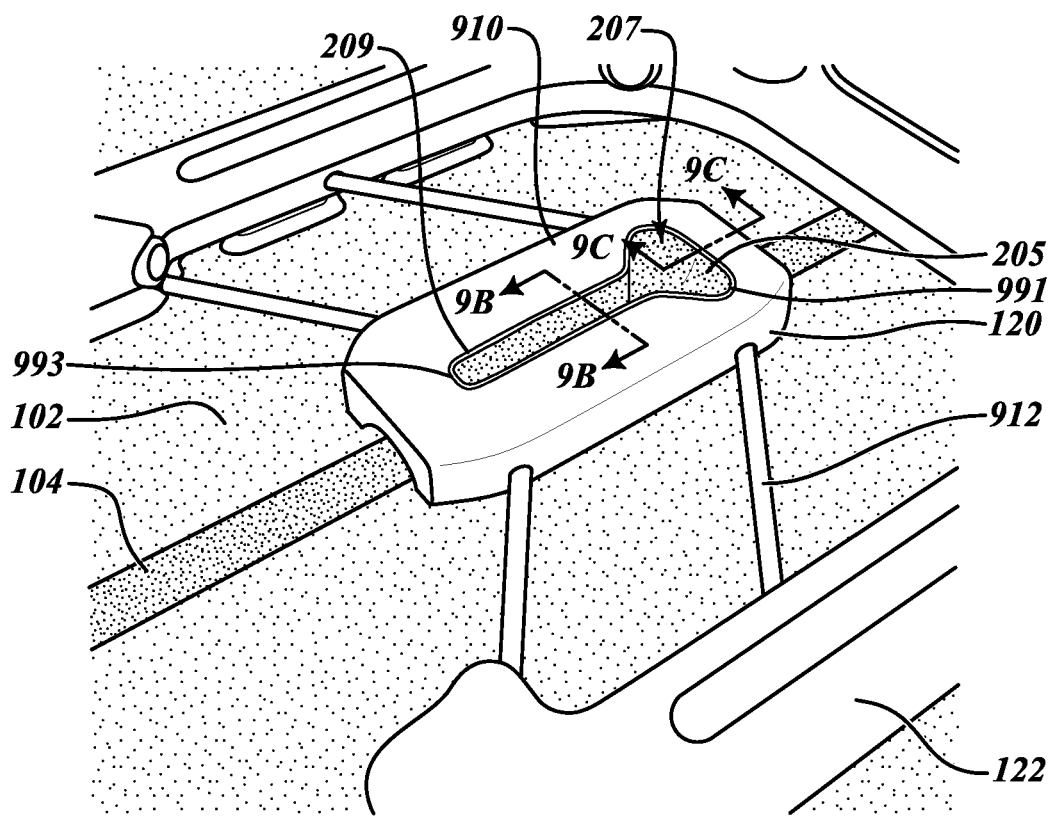
Figure 9B:
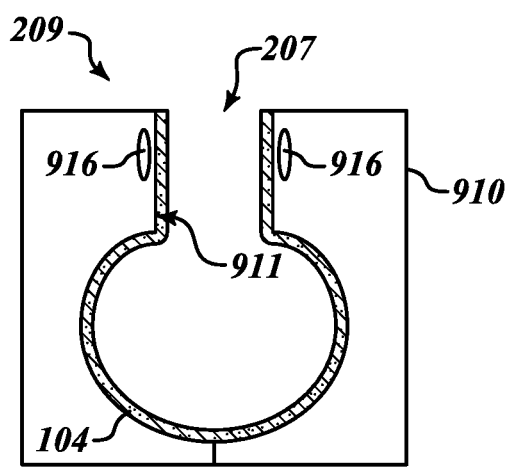
Figure 9C:
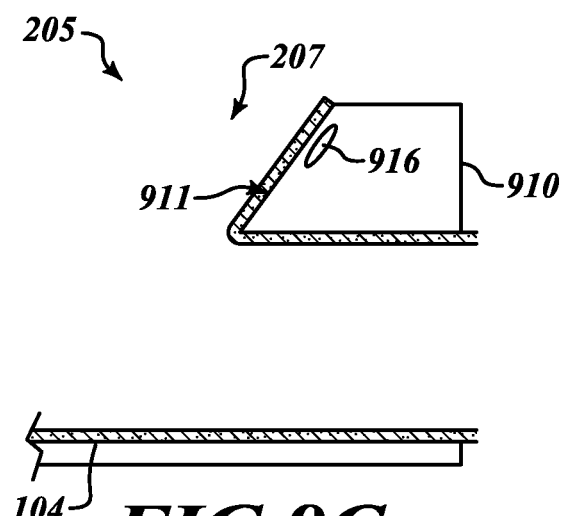
Figure 10A:
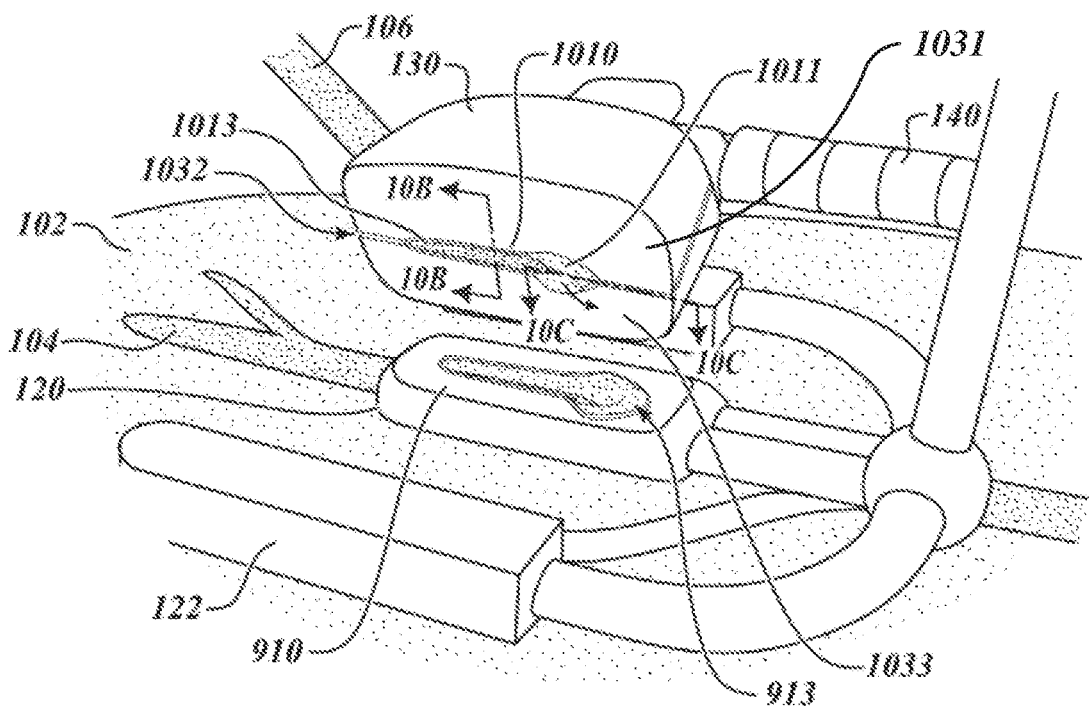
Figure 10B:
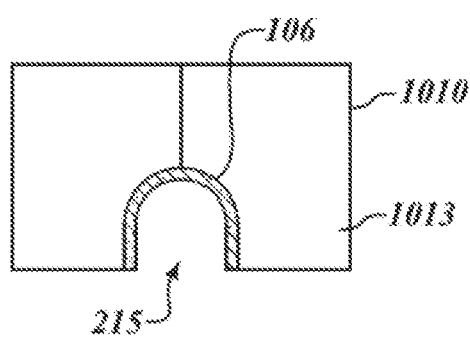
Figure 10C:
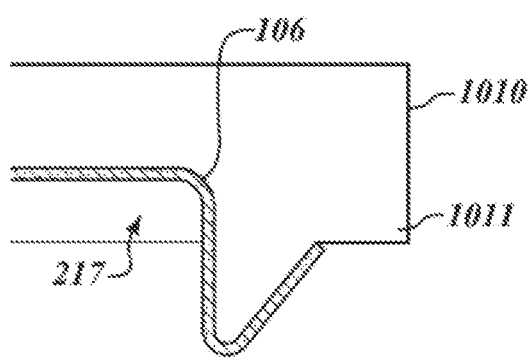
Figure 11A:
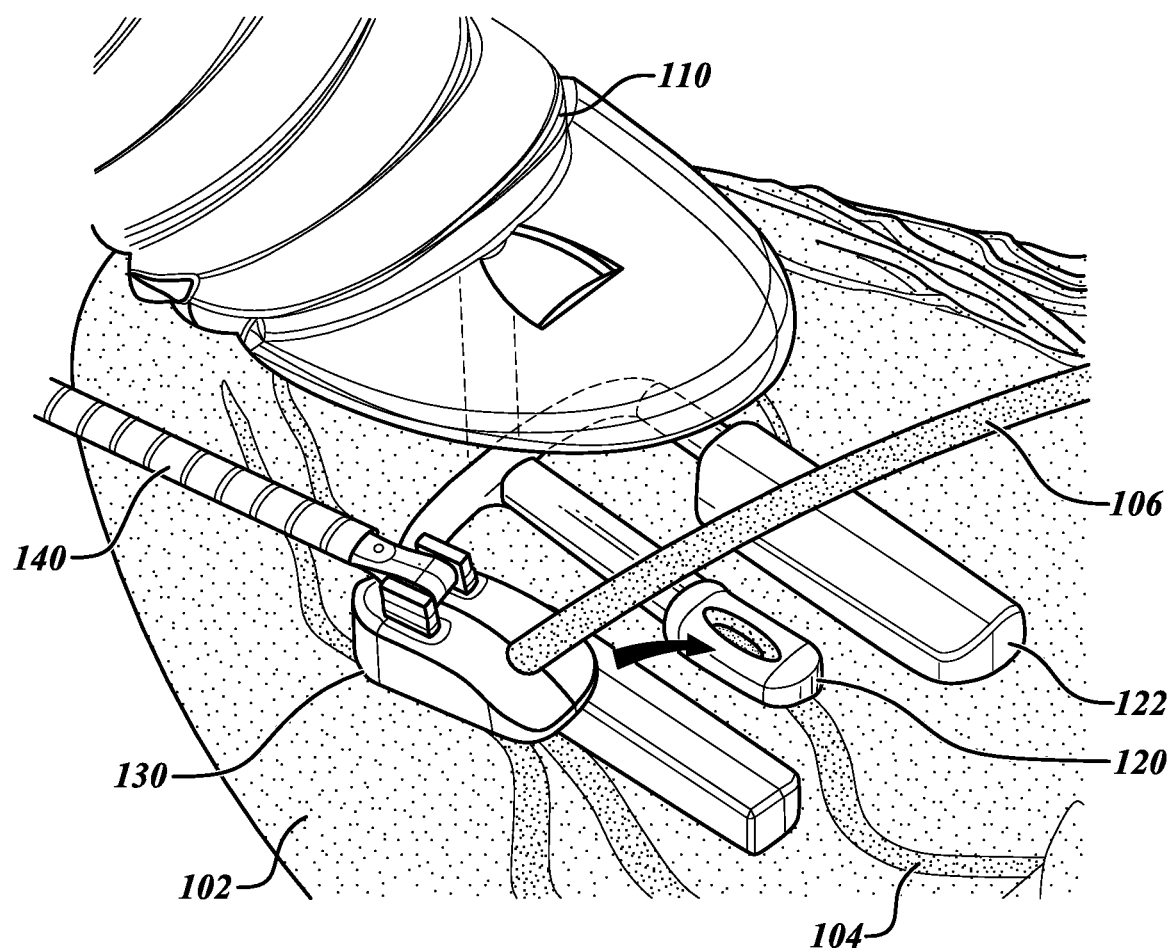
Figure 11B:
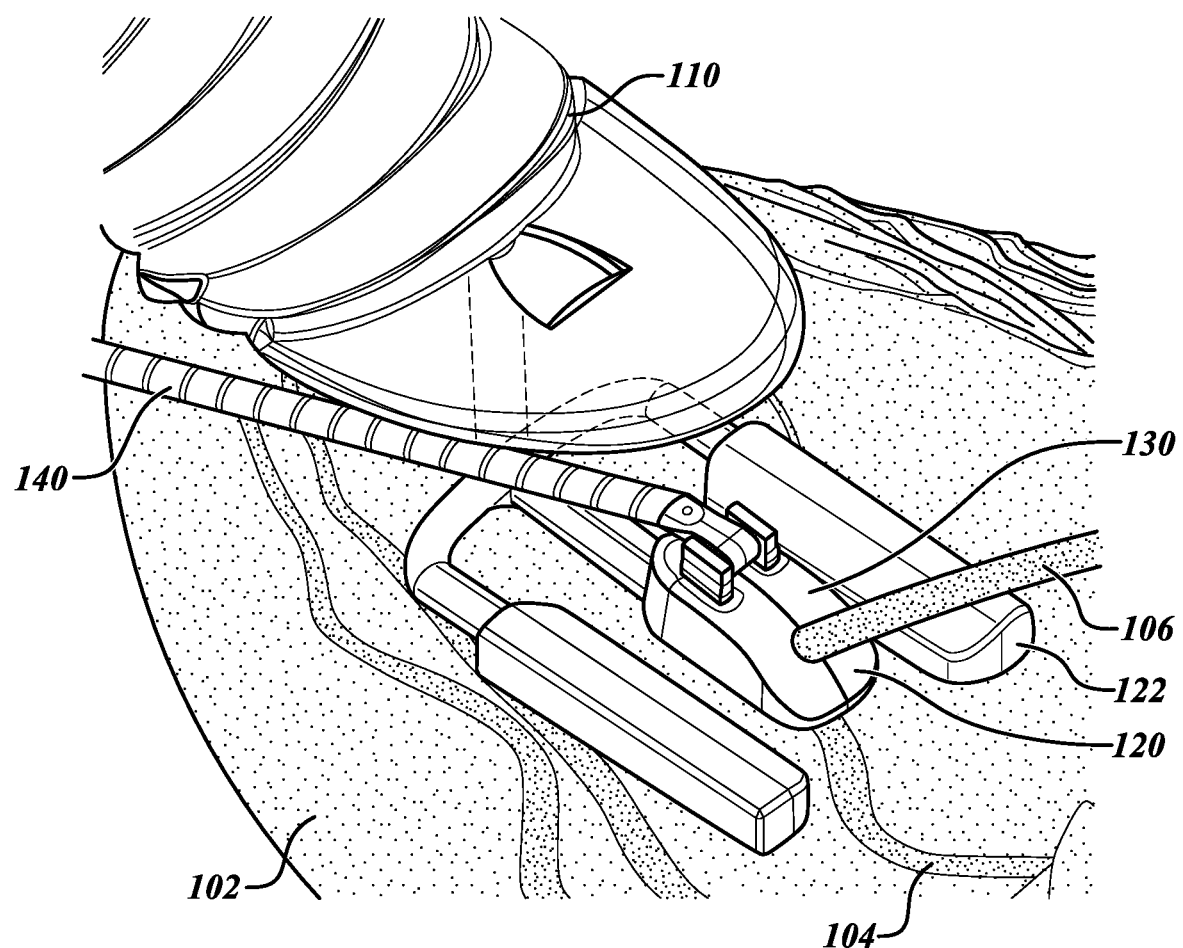
Figure 12:
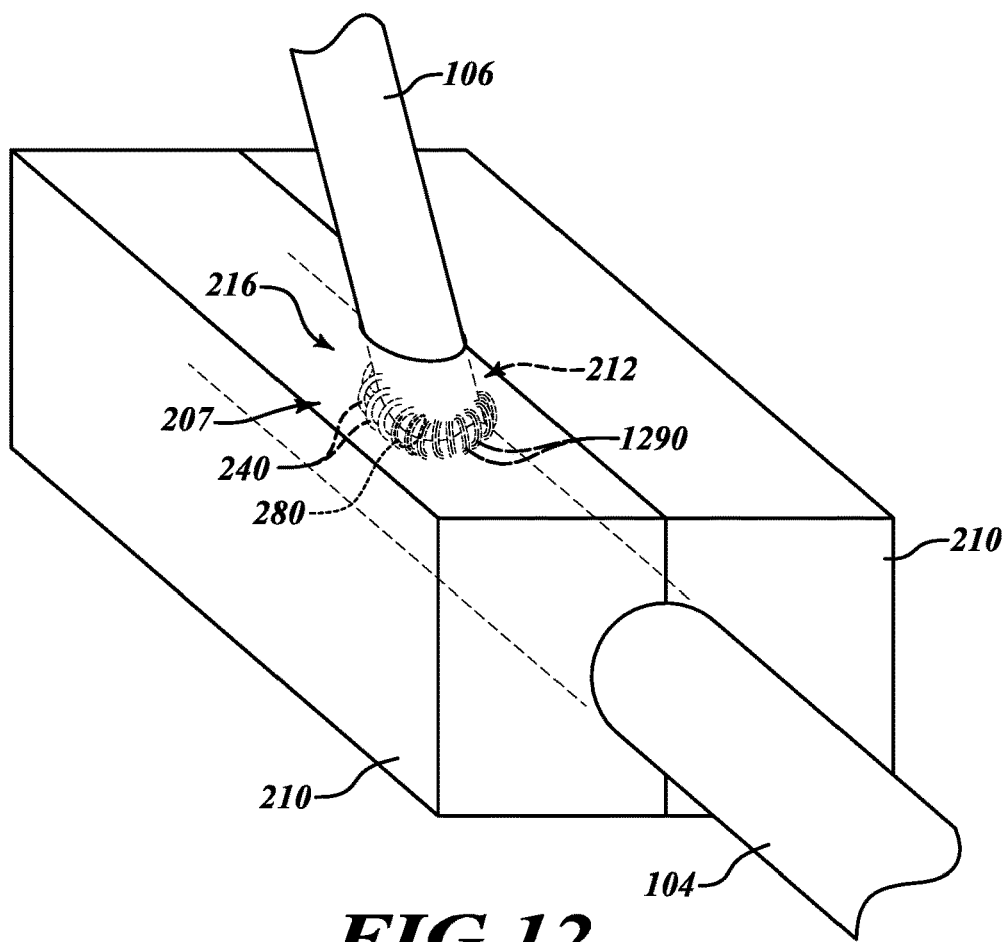
Figure 13:
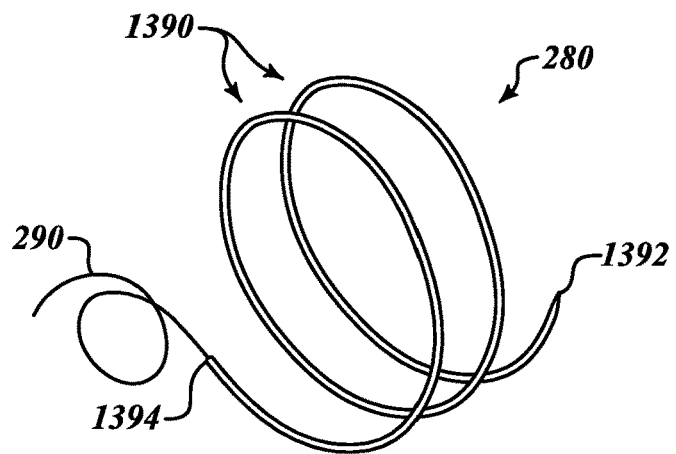
Figure 14:
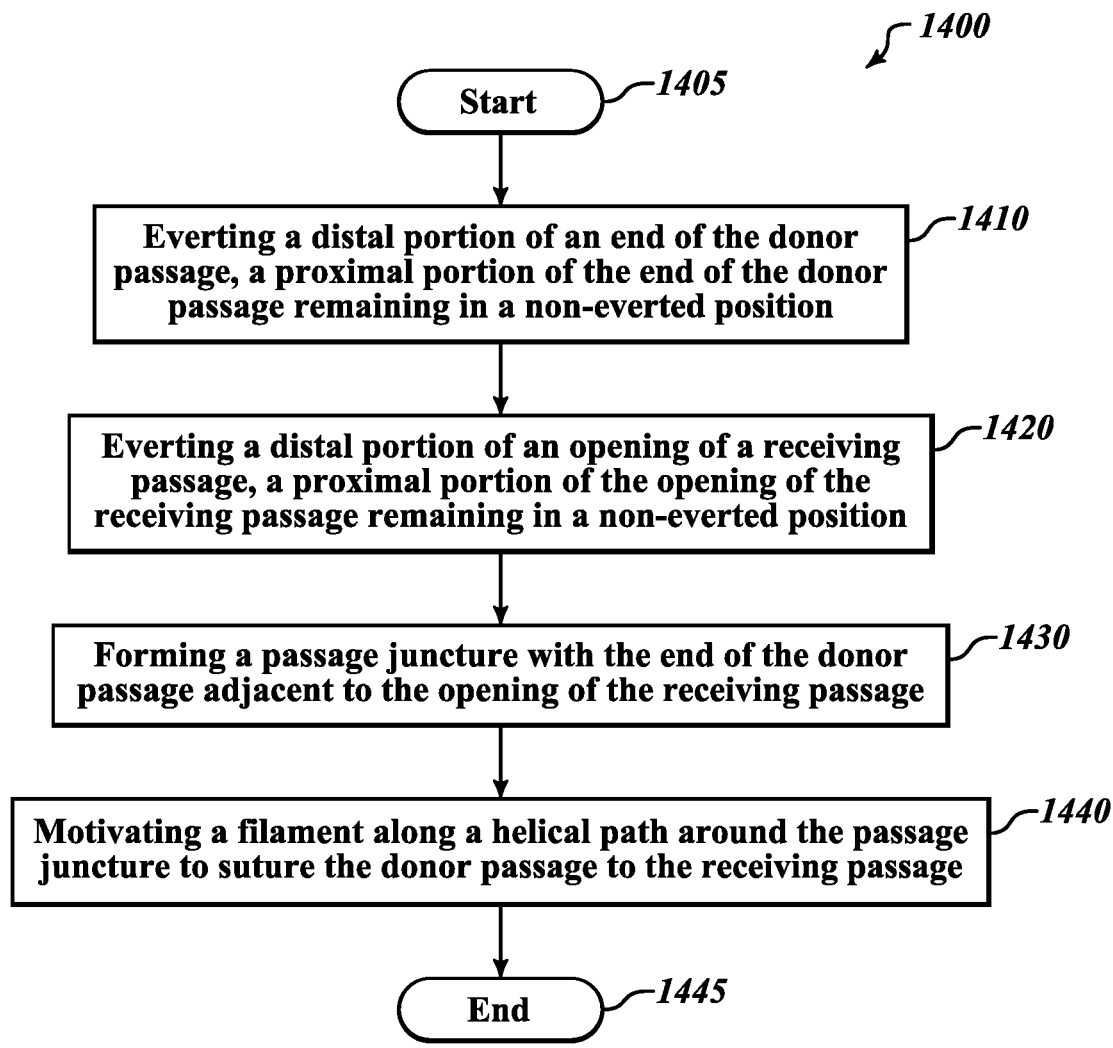

FIGS. 5A, 6A, and 7A are perspective views of the system of FIG. 1 disposed in various orientations on a heart;

FIGS. 5B, 6B, and 7B are perspective view of an eversion mechanism of the system of FIG. 1 as disposed on a heart corresponding to the perspective views of FIGS. 5A, 6A, and 7A, respectively;

FIG. 8 is a perspective view of the system of FIG. 1 positioned for formation of an opening in the receiving passage;

FIG. 9A is a perspective view of the eversion mechanism of the system of FIG. 1 used to evert the distal edge of the opening in the receiving passage;

FIG. 9B is a cross-sectional view of receiving passage in the eversion mechanism of FIG. 9A along a section B where the proximal edge of the opening in the receiving passage is not everted;

FIG. 9C is a cross-sectional view of receiving passage in the eversion mechanism of FIG. 9A along a section C where the distal edge of the opening in the receiving passage is everted;

FIG. 10A is a perspective view of the system of FIG. 1 showing the donor support mechanism moving the donor passage into position adjacent the receiving passage with a distal portion of the end of the donor passage everted;

FIG. 10B is a cross-sectional view of donor passage supported by the donor support mechanism of FIG. 10A along a section B where the proximal portion of the end of the donor passage is not everted;

FIG. 10C is a cross-sectional view of donor passage supported by the donor support mechanism of FIG. 10A along a section C where the distal portion of the end of the donor passage is everted;

FIG. 11A is a perspective view of the system of FIG. 1 in which the donor support mechanism is being moved toward against the eversion mechanism;

FIG. 11B is a perspective view of the system of FIG. 1 in which the donor support mechanism has been positioned adjacent the eversion mechanism to form a passage juncture between the donor passage and the receiving passage;

FIG. 12 is a perspective view of the suturing mechanism of FIG. 2 integrated into the system of FIG. 1 in partial cross-section for guiding a needle to suture both the non-everted portions and the everted portions of donor passage and the receiving passage at the passage juncture;

FIG. 13 is a perspective view of a helical needle that is moved along the generally helical path of the guide sections of FIG. 12 to suture the passage junction; and FIG. 14 is a flow diagram of an illustrative method of performing an anastomosis procedure according to the present disclosure.

DETAILED DESCRIPTION

The following description is merely illustrative in nature and is not intended to limit the present disclosure, application, or uses. It will be noted that the first digit of three-digit reference numbers, the first two digits of four-digit reference numbers correspond to the first digit of one-digit figure numbers and the first two-digits of the figure numbers, respectively, in which the element first appears.

The following description explains, by way of illustration only and not of limitation, various embodiments of noninvasive apparatuses, systems, and methods for positioning a receiving passage and a donor passage, and suturing the passages together in a surgical anastomosis procedure. The apparatuses, systems, and methods are described using the example of a CABG procedure involving the joining of a saphenous vein to a coronary artery in a CABG procedure. However, it will be appreciated that the same methods, apparatuses, and systems may be used for other grafting or anastomosis procedures for other arteries, intestines, or other bodily passages.

Referring to FIG. 1, in various embodiments and given by way of illustration only and not of limitation a system 100 is positioned on a patient's heart 102 at a receiving passage 104. In a non-limiting example given by way of illustration only and not of limitation, in various embodiments the receiving passage 104 is a coronary artery that may be involved in a CABG procedure. The system 100 includes a support body 110 that is configured to physically support and guide other components in a noninvasive anastomosis procedure, as further described below. The system 100 also includes an eversion mechanism 120 that is configured to engage and manipulate a portion of the receiving passage 104 that will become the receiving passage in the CABG procedure, as further described below. As also described further below, the eversion mechanism 120 is configured to invert only a portion of an edge around an opening (not shown in FIG. 1) to be formed in the receiving passage 104. The everted portion of the opening in the receiving passage 104 will engage an everted portion of an end (not shown in FIG. 1) of a donor passage 106. Non-everted portions of the receiving passage 104 will be joined to non-everted portions of the end of the donor passage 106, as further described below. The eversion mechanism 120 may include a stabilizer 122 to secure a position of the heart 102 and maintain a position of the eversion mechanism 120 and the rest of the system 100 relative to the heart 102.

In various embodiments the system 100 also includes a donor support mechanism 130 configured to support the donor passage 106. In non-limiting examples included in this description, the donor passage 106 may be a saphenous vein that may be involved in a CABG procedure. In such embodiments, the donor support mechanism 130 is used to move the donor passage 106 into position relative to the receiving passage 104 for grafting, as described further below. A suturing mechanism (not shown in FIG. 1) that is operably coupled with the eversion mechanism 120 and the donor support mechanism 130 is used to suture the donor passage 106 to the receiving passage 104, as also described further below with reference to FIG. 2 and other figures. In an illustrative embodiment, a control conduit 140 is coupled with the donor support mechanism 130 for controlling the suturing to complete the graft, as described below.

As previously stated, although this description will use for purposes of illustration the non-limiting example of a CABG procedure, it will be appreciated that the same apparatuses, systems, and methods may be used for other anastomosis procedures. Accordingly, in the interest of simplicity, the following description refers only to the example of the donor passage 106 being grafted to the receiving passage 104, although similar procedures may be performed with other donor passages and receiving passages.

Referring to FIG. 2, in various embodiments a suturing mechanism 200 includes one or more sets of guide sections 210 that are disposed around an outside of a passage juncture 212 formed by surfaces of the receiving passage 104 and the donor passage 106. More specifically, in forming the passage juncture 212, a distal edge 205 of an opening 207 formed in the receiving passage 104 is everted, as described below with reference to FIGS. 8, 9A, and 9C. The distal edge 205 is so designated because of its relative position to a source of blood flow 254 in the receiving passage 104, represented by an arrow in FIG. 2. The distal edge 205 is relatively further removed from the source of the blood flow 254 than a proximal edge 209. The proximal edge 209 is not everted.

In forming the passage juncture 212, in various embodiments a distal portion 217 of an end 216 of the donor passage 106 is also everted—where it will be joined to the distal edge 205 of the receiving passage 104. As in the case of the receiving passage 104, the distal portion 217 of the end 216 of the donor passage is referred to as being distal because of its relative position to a source of blood flow 256 in the donor passage 206, represented by an arrow in FIG. 2. The distal portion 217 is relatively further removed from the source of the blood flow 256 than a proximal portion 215 of the end 216 of the donor passage 106. The proximal portion 215 is not everted.

In various embodiments the one or more sets of guide sections 210 are shaped to surround an outside of passage juncture 212 formed at the end 216 of the donor passage 106 and the opening 207 in the receiving passage 104. An interior surface 221 of the everted distal portion 217 of the end 216 of the donor passage 106 is positioned against an interior surface 211 of the everted distal edge 205 of the receiving passage 104. The non-everted proximal portion 215 of the end 216 of the donor passage 106 is positioned against the non-everted proximal edge 209 of the opening 207 in the receiving passage 104. The non-everted proximal portion 215 and the non-everted proximal edge 209 may present a less bulky juncture as compared with the juncture formed by the interior surface 221 positioned against the interior surface 211. As a result, the joint of the non-everted proximal portion 215 and the non-everted proximal edge 209 may help present a reduced impairment in a flow of blood into the passage juncture 212 from sources of the blood flow 254 and 256.

In various embodiments inner faces 223 of the guide sections 210 present a partial helical channel 240 along which a needle is motivated to draw a filament to suture the passage juncture 212, as described further below with reference to FIGS. 12 and 13. Although not shown in FIG. 2, the guide sections 210 may be joined to or formed integrally with the donor support mechanism 130 and/or they may be part of a stand-alone suturing mechanism 200.

Figure 3:
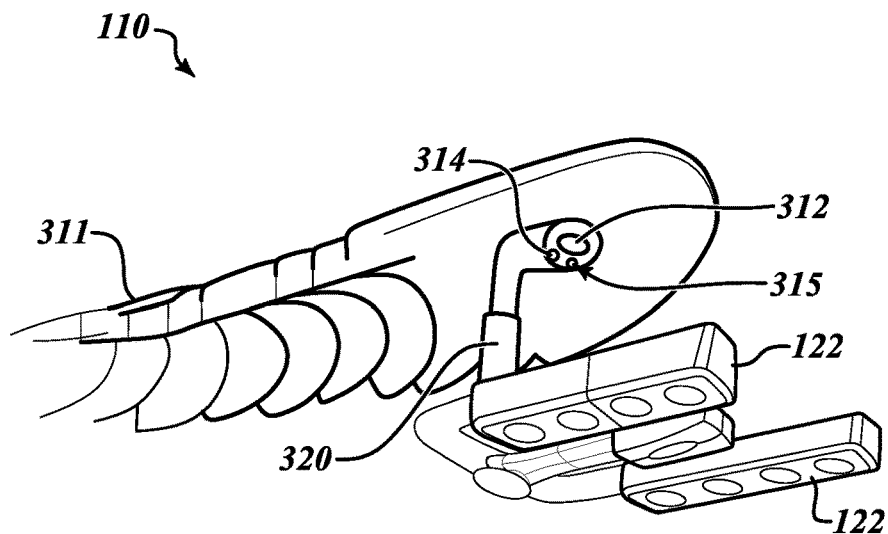
FIG. 3 is a perspective view of the system of FIG. 1 shown from an underside prior to being positioned to perform a procedure.

Referring to FIG. 3, in various embodiments an underside of the support body 110 supports the eversion mechanism 120 and the stabilizer 122. The eversion mechanism 120 and the stabilizer 122 may be coupled to the support body 110 with a bracket 320. The support body 110 includes a handle 311 that enables an operator (not shown in FIG. 3) to insert the support body 110 through an opening such as may be formed by an incision, as further described below with reference to FIG. 4. After inserting the support body 110 into the opening, the operator can then manipulate the handle 311 to position the support body 110 and, thus, the attached eversion mechanism 120 and stabilizer 122. The operator can withdraw the same after the procedure is completed. The handle 311 also may convey to the support body 110 and the bracket 320 tubing and/or wiring (not shown) to control operation of the system.

In various embodiments, the support body 110 also may include other components to assist the operator in performing the procedure. In various embodiments, the support body 110 may include an optical system 315 to aid the operator in guiding the support body 110 to a desired location and completing the procedure. The optical system 315 may include a camera 312 to provide imaging data, via a wired or a wireless connection, to a display (not shown) that may be viewed by the operator. The optical system 315 also may include a light source 314 to provide illumination in the vicinity of the support body to facilitate capturing useful optical imaging data with the camera 312.

Figure 4:
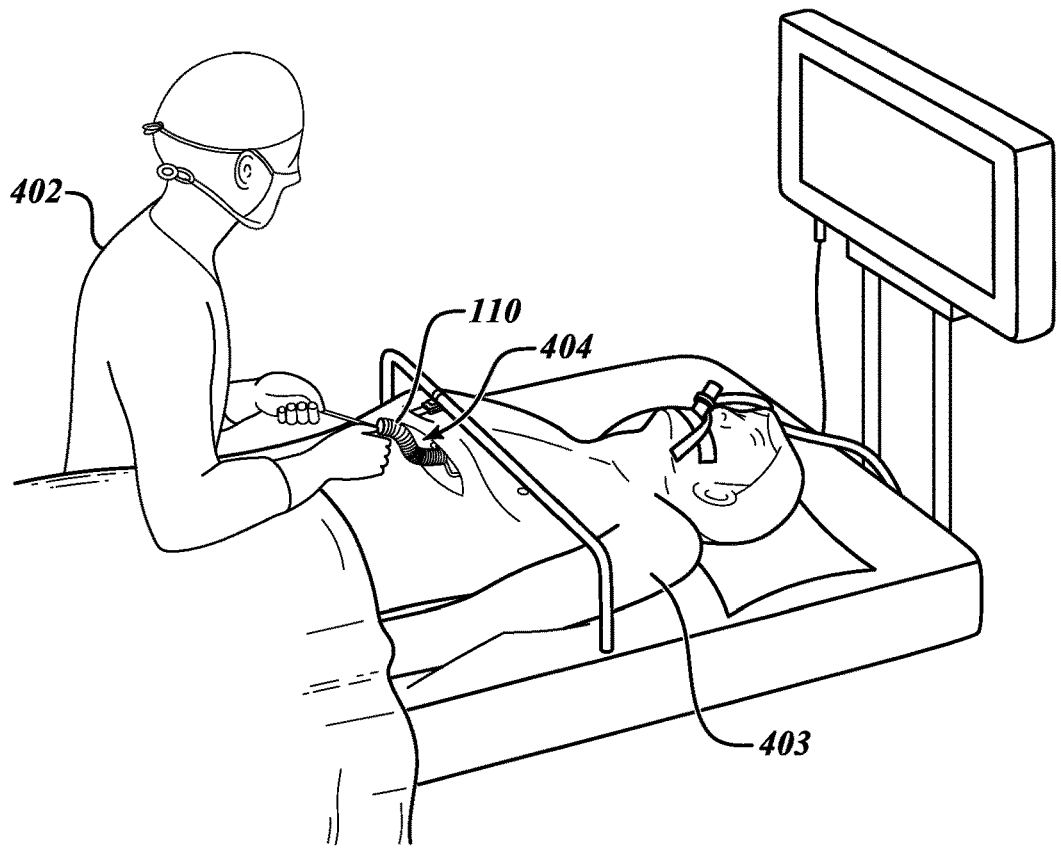
FIG. 4 is a perspective view showing insertion of the system of FIG. 1 into a patient for performance of the CABG procedure.

Referring to FIG. 4, in various embodiments an operator 402 deploys the support body 110 (and its associated components) to perform a procedure on a patient 403. In the example of a CABG procedure, the support body 110 may be deployed through a subxiphoid incision 404 made below the sternum of the patient 403. Using the system 100 and manipulating the support body 110 and its associated components, the operator 402 may be able to perform a procedure on the patient 403 with minimal invasiveness. For example, in the case of a CABG procedure, a conventional procedure would involve a median sternotomy with one or more lengthy incisions and the dividing of the sternum; by contrast, using the system 100, the operator may be able to perform the CABG procedure through the much less invasive subxiphoid incision 404 as shown in FIG. 4.

Referring to FIGS. 5A-7B and continuing with the example of a CABG procedure, in various embodiments the system 100 can help facilitate performance of a CABG procedure at different locations on the surface of the heart 102. Referring to FIGS. 5A and 5B, the support body 110 is positioned to perform a CABG procedure on an anterior surface 501 of the heart 102. A positioning device 505 may be inserted through the same subxiphoid incision 404 through which the support body 110 is inserted into the body. The positioning device 505 may be used to lift or otherwise position the heart 102 and hold it in place while the CABG procedure is performed. The positioning device 505 may be situated with the aid of the optical system 315 on the support body 110 (FIG. 3). The handle 311 may be manipulated by the user to direct the support body 110 to a desired location on the heart 102. Surgical tools, such as an endoscopic scalpel 591 and a manipulating tool 593, such as a probe or a pair of forceps, may be used in connection with the system 100 to complete the procedure, as described further below.

Referring to FIGS. 6A and 6B, in various embodiments the support body 110 is positioned on a lateral surface 601 of the heart 102. As compared to the situation depicted in FIGS. 5A and 5B, performing a procedure on the lateral surface 610 of the heart 102 may not involve moving the heart 102 with the positioning device 505 (FIG. 5A). However, various embodiments of the support body 110 permit rotation of the eversion mechanism 120 and the stabilizer 122 relative to the support body 110 to facilitate disposing the eversion mechanism 120 and the stabilizer 122 on the lateral surface 601 of the heart 102.

Referring to FIGS. 7A and 7B, the support body 110 also may be positioned on an inferior surface 701 of the heart 102. Performing a CABG procedure on the interior surface 701 of the heart 102 may not necessitate rotation of the eversion mechanism 120 and the stabilizer 122 or use of a positioning device 505. The handle 311 may be manipulated by the user to direct the support body 110 to a desired location on the heart 102.

Referring to FIG. 8, in various embodiments the CABG procedure proceeds with securing the eversion mechanism 120 and the stabilizer 122 in place on the heart 102 followed by making an incision in the receiving passage 104. To proceed with the CABG procedure, the eversion mechanism 120 is situated directly over the receiving passage 104 that is to receive the graft, such as from a saphenous vein or other donor passage (not shown in FIG. 8). The stabilizer 122 is then secured to the surface of the heart 102 to hold the eversion mechanism 120 in place. The stabilizer 122 may be connected to a vacuum source (not shown), such as through the control conduit 140 (FIG. 1), so that openings in an underside of the stabilizer 122 may grip the heart 102 to hold the stabilizer 122 and, in turn, the eversion mechanism 120 in place on the heart 102. Alternatively, the stabilizer 122 may include mechanical grips, such as prongs, to anchor the stabilizer 120 to the heart 102.

Once the eversion mechanism 120 is thus secured in place, a clamp or suture (not shown) may be applied to the receiving passage 104 ahead of the location where the eversion mechanism 120 has been positioned (where "ahead" is used to denote the clamp or suture being situated to block the blood flow to the portion of the receiving passage 104 where the eversion mechanism 120 is situated). Alternatively, blood flow may be stopped by the application of a tourniquet or another technique of applying direct external pressure to the receiving passage 104.

After the blood flow has been stopped, the opening 207 is formed in the receiving passage 104 within the area bounded by the eversion mechanism 801. The opening 207 may be formed by, for example, making an incision in the receiving passage 104, such as by using an endoscopic scalpel 591. The endoscopic scalpel 591 or other cutting tool (not shown) may be inserted through the same subxiphoid incision 404 through which the support body 110 was inserted. The formation of the opening 207, such as by using the endoscopic scalpel 591, may be guided by the optical system 315 (FIG. 3) on the support body 110.

Referring to FIG. 9A and in various embodiments, after the incision is made to form the opening 207, the eversion mechanism 120 is used to evert the distal edge 217 of the opening 207 in the receiving passage 104 to prepare the receiving passage 104 to receive the saphenous vein or other donor passage (not shown in FIG. 9A). As previously described, in various embodiments, the eversion mechanism 120 may employ suction from an external source to engage the distal edge 205 of the opening 207 and to draw the distal edge 205 to a rim 910 of the eversion mechanism 120 at a distal end 991 of the rim 910. For example, suction may be applied from a vacuum source (not shown) outside the body and conveyed via the control conduit 140 (FIG. 1) to the eversion mechanism 120 to the openings 916 (FIGS. 9B and 9C) in the rim 910. The suction may be applied to the rim 910 via conduits 912 extending between the stabilizer 122 and the rim 910. The manipulating tool 593 (not shown in FIG. 9A) may be used to push or prod the edges 205 toward the rim 910 to aid the suction applied through the rim 910 in taking hold of the distal edge 207 along the opening 207 of the receiving passage 104. Suction The proximal edge 209 along the opening 207 of the receiving passage 104 also may be secured in place at a proximal end 993 of the rim 910, such as by applying suction through openings 916 (FIG. 9B) in the rim. However, the proximal edge 209, as previously described with reference to FIG. 2, is not everted along the opening 207 in the receiving passage 104.

Referring to FIG. 9B, the proximal edge 209 of the opening 207 of the receiving passage 104, as previously described with reference to FIG. 2, is not everted. The rim 910 may engage external sides 911 of the proximal edge 209, such as by using suction applied through the openings 916 to hold external sides 911 of the receiving passage 104 in place.

Referring to FIG. 9C, external sides 911 of the distal edge 205 of the receiving passage 104 are drawn toward the openings 916 in the rim 910. By comparison with FIG. 9B, it will be appreciated that the shape of the distal edge 991 of the rim everts the distal edge 205 of the receiving artery 104 while the proximal edge 209 remains non-everted. The rim 910 holds the distal edge 205 and the proximal edge 209 of the receiving passage 104 in place to receive the end 216 of the donor passage 106 (FIG. 2).

Referring to FIG. 10A and in various embodiments, the donor support mechanism 130 is used to position the donor passage 106, such as a saphenous vein. The eversion mechanism 120 and the stabilizer 122 are put in place over the receiving passage 104 on the heart 102, with the eversion mechanism 120 everting the distal edge 205 of the receiving passage 104 to prepare for grafting as previously described. The donor passage 106 is then positioned on the donor support mechanism 130. Because the donor passage 106 is removable (and has been harvested from another location in the patient's body to perform the CABG procedure), the donor passage 106 may be manually positioned on an end 1010 of the donor support mechanism 130. A distal portion 1011 of the end 1010 of the donor support mechanism 130 is shaped to support the distal portion 217 of the end 216 of the donor passage 106 in an everted position. A proximal portion 1013 of the end 101 of the donor support mechanism 130 is shaped to support the proximal portion 215 of the end 216 of the donor passage 106 in a non-everted position.

Referring to FIG. 10B, in various embodiments the proximal portion 215 of the end 216 of the donor passage 104, as previously described with reference to FIGS. 2 and 10A, is not everted. The proximal portion 215 may be held in place by the proximal portion 1013 of the end 1010 of the donor support mechanism 130, but the proximal portion 215 is not everted.

Referring to FIG. 10C, the distal portion 217 of the end 216 of the donor passage 106 is held in place by the distal portion 1011 of the end 1010 of the donor support mechanism 130 in an everted position. By comparison with FIG. 10B, it is the shape of the distal portion 1011 that presents the distal portion 217 in an everted position. The end 1010 of the donor support mechanism 130 holds the distal portion 217 and the proximal portions 215 of the donor passage 106 in place to be positioned against the opening 207 of the donor passage 106 (FIG. 2) for grafting.

Referring again to FIG. 10A, in various embodiments the donor support mechanism 130 includes two segments 1031 and 1033 that meet at a joint 1032. The two segments 1031 and 1033 are held together when the donor passage 106 is inserted into the donor support mechanism 130 and the edges 209 of the end 211 of the donor passage 106 are drawn back over the end 1010 of the donor support mechanism 130. After the donor passage 106 is sutured to the receiving passage 104, the segments 1031 and 1033 are removed from one another at the joint 1032 and removed from around the donor passage 106. Thus, the donor support mechanism 130 is removable after the CABG procedure, thereby leaving the sutured donor passage 106 in place. The segments 1031 and 1033 may incorporate the guide sections 210 (not shown in FIG. 10A) for facilitating the suturing of the graft.

Referring to FIGS. 11A and 11B, in various embodiments the donor support mechanism 130 is moved into place over the eversion mechanism 120 to perform the CABG procedure. Referring to FIG. 11A, the donor support mechanism 130 supports the donor passage 106 to prepare for the anastomosis procedure. Referring to FIG. 11B, the donor support mechanism 130 is moved into place over the eversion mechanism 120 to form the passage juncture 212. The donor passage 106 may then be sutured to the receiving passage 104 to complete the CABG procedure.

Referring to FIG. 12, in various embodiments the guide sections 210 of the suturing mechanism 200 are positioned around a periphery of the passage juncture 212 formed by the end 216 of the donor passage 206 and the opening 207 in the receiving passage 104. In various embodiments, the guide sections 210 are mounted on or integrally formed as part of the donor support mechanism 130. Thus, when the donor support mechanism 130 (to which the donor passage 106 is secured as previously described with reference to FIGS. 10A-10C) is moved into place over the eversion mechanism 120 (to which the receiving passage 104 is secured as described with reference to FIGS. 9A-9C), the passage juncture 212 formed thereby is ready to be sutured. The partial helical channel 240 defined in the faces 223 of the guide sections 210 (FIG. 2) surrounds the passage juncture 212 from the outside. With the partial helical channel 240 in place around an outside of the passage juncture 212, the helical needle 280 is motivated along the partial helical channel 240 to complete the graft with sutures 1290.

Referring to FIG. 13, in various embodiments the helical needle 280 is configured to conform to the partial helical channel 240. A pointed leading end 1392 is configured to pierce the tissue of the receiving passage 104 and the donor passage 106 as the helical needle 280 moves along the partial helical channel 240. A trailing end 1394 is coupled with or configured to be attached to a filament 290. The needle 280 is thus able to direct the filament 290 along a helical path to suture the receiving passage 104 and the donor passage 106 to complete the grafting procedure.

Referring to FIG. 14, in various embodiments an illustrative method 1400 of performing an anastomosis procedure is provided. The method 1400 starts at a block 1405. At a block 1410, a distal portion of an end of the donor passage is everted, while a proximal portion of the end of the donor passage remains in a non-everted position. At a block 1420, a distal portion of an opening of a receiving passage is everted, while a proximal portion of the opening of the receiving passage remains in a non-everted position. At a block 1430, a passage juncture is formed with the end of the donor passage adjacent to the opening of the receiving passage. At a block 1440, a filament is motivated along a generally helical path around the passage juncture to suture the donor passage to the receiving passage. The method 1400 ends at a block 1445, with the passage juncture sutured together to complete the grafting of the donor passage and the receiving passage.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
    an eversion mechanism configured to partially evert a distal portion of an opening of a receiving passage and further configured to leave a proximal portion of the opening of the receiving passage in a non-everted position;
    a donor support mechanism configured to partially evert a distal portion of an end of a donor passage and further configured to leave a first proximal portion of the end of the donor passage in a non-everted position, the donor support mechanism being further configured to form a passage juncture at the end of the donor passage and the opening of the receiving passage; and
    a suturing mechanism configured to motivate a filament through a generally helical path around the passage juncture to suture the donor passage to the receiving passage.

2. The apparatus of claim 1, wherein the first proximal portion of the end of the donor passage is configured to meet the proximal portion of the receiving passage at an acute angle.

3. The apparatus of claim 1, wherein the eversion mechanism includes a first suction device configured to apply suction to an external surface of at least the distal portion of the opening of the receiving passage.

4. The apparatus of claim 1, wherein the suturing mechanism further comprises a plurality of guide sections, wherein an interior surface of each guide section defines a partial helical channel.

5. The apparatus of claim 4, further comprising a helical needle configured to receive an end of a suture and further configured to conform to the partial helical channel defined by the interior surface of each guide section as the helical needle is motivated through the plurality of guide sections to suture the passage juncture.

6. The apparatus of claim 1, further comprising a stabilizer configured to support the suturing mechanism against a body passage adjacent the opening of the receiving passage.

7. A system comprising:
    a support body configured to be inserted into a body;
    a camera system operably coupled with the support body, wherein the camera system is configured to convey imaging data from the support body to an operator;
    an eversion mechanism configured to partially evert a distal portion of an opening of a receiving passage and further configured to leave a proximal portion of the opening of the receiving passage in a non-everted position;
    a donor support mechanism configured to partially evert a distal portion of an end of a donor passage and further configured to leave a first proximal portion of the end of the donor passage in a non-everted position, the donor support mechanism being further configured to form a passage juncture at the end of the donor passage and the opening of the receiving passage; and
    a suturing mechanism configured to motivate a filament through a generally helical path around the passage juncture to suture the donor passage to the receiving passage.

8. The system of claim 7, wherein the first proximal portion of the end of the donor passage is configured to meet the proximal portion of the receiving passage at an acute angle.

9. The system of claim 7, wherein the eversion mechanism includes a first suction device configured to apply suction to an external surface of at least the distal portion of the opening of the receiving passage.

10. The system of claim 7, wherein the suturing mechanism further comprises a plurality of guide sections, wherein an interior surface of each guide section defines a partial helical channel.

11. The system of claim 7, further comprising a helical needle configured to receive an end of a suture and further configured to conform to the partial helical channel defined by the interior surface of each guide section as the helical needle is motivated through the plurality of guide sections to suture the passage juncture.

12. The system of claim 7, further comprising a stabilizer configured to support the suturing mechanism against a body passage adjacent the opening of the receiving passage.

\* \* \* \* \*